United States Patent [19]

Yamamoto et al.

[11] Patent Number: 5,106,625
[45] Date of Patent: Apr. 21, 1992

[54] COMPOSITION FOR EXTERNAL APPLICATION CONSISTING ESSENTIALLY OF A DEXTRIN FATTY ACID ESTER, A GLYCEROL FATTY ACID ESTER AND AN OIL

[75] Inventors: Tomoyuki Yamamoto; Akira Shigeta, both of Tokyo; Yuichiro Mitsuno, Sakura, all of Japan

[73] Assignee: Kao Corporation, Tokyo, Japan

[21] Appl. No.: 564,063

[22] Filed: Aug. 8, 1990

[30] Foreign Application Priority Data

Aug. 9, 1989 [JP] Japan .................................. 1-206546

[51] Int. Cl.$^5$ ................................................ A61K 7/48
[52] U.S. Cl. ....................................... 424/401; 424/47; 424/59; 424/63; 514/943
[58] Field of Search .................. 424/401, 47; 514/777, 514/943; 426/602

[56] References Cited

U.S. PATENT DOCUMENTS

| | | | |
|---|---|---|---|
| 4,093,745 | 6/1978 | Wood | 424/69 |
| 4,305,961 | 12/1981 | Tsutsumi et al. | 514/777 |
| 4,379,755 | 4/1983 | Yamada et al. | 426/602 |
| 4,791,140 | 12/1988 | Fukasawa | 514/944 |
| 4,897,261 | 1/1990 | Yamazaki | 424/61 |
| 4,931,210 | 6/1990 | Takahashi | 424/70 |

Primary Examiner—Thurman K. Page
Assistant Examiner—D. Colucci
Attorney, Agent, or Firm—Oblon, Spivak, McClelland, Maier & Neustadt

[57] ABSTRACT

An oily composition comprising a dextrin fatty acid ester, a glycerol fatty acid ester having a melting point of higher than 20° C., and a liquid oil is disclosed. The oily compositions for external application are transparent or semi-transparent, and possess excellent extendibility, adhesive capability, and retentivity on the skin. The compositions are useful for various oily cosmetics and oily medicines for external application.

11 Claims, No Drawings

COMPOSITION FOR EXTERNAL APPLICATION CONSISTING ESSENTIALLY OF A DEXTRIN FATTY ACID ESTER, A GLYCEROL FATTY ACID ESTER AND AN OIL

BACKGROUND OF THE INVENTION

1. Field of the Invention

This invention relates to an oily composition for external application having transparent or semi-transparent appearance and providing excellent retentivity and extendibility on the skin and adhesive capability to the skin.

2. Description of the Background Art

Oily compositions for external application include, for example, oily cosmetics, oily medicines for external application, and the like. Typical examples of oily cosmetics are stick-type cosmetics, e.g. lipsticks, lipcreams, foundation sticks, stick pomade; pencil-type cosmetics, e.g. eyebrow pencil, eyeliner pencil; and pressed powders and oily cake-type cosmetics, e.g. foundations, eyeshadows, rouges. Examples of oily medicines for external application are ointments and the like.

These oily cosmetics are usually prepared by mixing solid fats such as carnauba wax, candelilla wax, ceresine, microcrystalline wax, hydrogenated animal or vegetable fats, bees wax, polyethylene wax, and the like with oils such as castor oil, olive oil, jojova oil, squalane, various synthetic esters, silicone oil, liquid paraffin, and the like, into which powders such as pigments and the like are dispersed as required. There are some oily cosmetics in which semi-solid oils such as vaseline and the like, which show an intermediate characteristics of solid fats and liquid oils, are used in place of the above oil components. Oily medicines for external application are usually produced by kneading pharmaceutical components into the mixed system of the above solid fats and liquid oils.

The oily composition produced from a mixed system of the above solid fats and liquid oils, however, has namely a curd-house structure in which crystals of the solid fats precipitates from the oils of liquid-state. This type of crystals is hard to control and becomes large in size. Hence, oily compositions have resultantly poor transparency and tend to become turbid. In addition, oily compositions must incorporate a relatively greater amount of solid fats for the improvement of shape-retentivity. Such compositions usually become hard, have poor extendibility on the skin, and possess a poor adhesive capability because they lose their uniform structure when applied to. Further, one of the drawbacks of those compositions is that the retentivity of the compositions is reduced after they are applied to the skin because the viscosities of the compositions are lowered.

Therefore, this invention is directed to an oily composition for external application having transparent or semi-transparent appearance and providing excellent retentivity and extendibility on the skin and adhesive capability to the skin.

In view of this situation, the present inventors have conducted extensive studies, and consequently, found that an oily composition for external application having transparent or semi-transparent appearance and providing excellent extendibility and adhesive capability can be obtained by incorporating two kinds of specific fatty acid esters and liquid-state oils in a specific proportion. This finding has led to the completion of the present invention.

SUMMARY OF THE INVENTION

Accordingly, an object of the present invention is to provide a transparent or semi-transparent oily composition for external application having an excellent retentivity and extendibility and adhesive capability to the skin comprising (A) a dextrin fatty acid ester, (B) a glycerol fatty acid ester having a melting point of higher than 20° C., and (C) a cosmetiaclly acceptable oil which is liquid at 20° C.

In a preferred embodiment of the present invention, said dextrin fatty acid ester (A) is an ester of a dextrin of an average polymerization degree of 10 to 50 and a fatty acid having 8-24 carbon atoms, said glycerol fatty acid ester (B) has a melting point of higher than 20° C. and a fatty acid residue with a carbon atom content of 8-22, and a ratio of (A):(B) is from 9:1-4:6 by weight, and the total weight of (A) and (B) is 2-75% by weight.

Other objects, features and advantages of the invention will hereinafter become more readily apparent from the following description.

DETAILED DESCRIPTION OF THE INVENTION AND PREFERRED EMBODIMENTS

The dextrin fatty acid esters used in this invention are of oil-soluble and preferably those ester compounds of (1) a fatty acid having 8-24 carbon atoms, more preferably 14-18 carbon atoms, and (2) a dextrin of an average polymerization degree of 10 to 50, more preferably those of 20-30. A preferable substitution degree of fatty acids is not less than 1.0 per one glucose unit.

Examples of these dextrin fatty acid esters are dextrin palmitate, dextrin stearate, dextrin palmitate stearate, dextrin oleate, dextrin isopalmitate, dextrin isostearate, and the like. They can be used singly or as a mixture of one or more of them. A preferable dextrin fatty acid ester which is commercially available is dextrin palmitate (Leopal KL, produced by Chiba Seifun Co., Ltd.).

Glycerol fatty acid esters used in this invention are those having a melting point of higher than 20° C. Among them, mono-, di-, or tri-glycerol fatty acid esters having a melting point of higher than 30° C. and a fatty acid residue carbon number of 8-22 are preferable. Preferable examples of these glycerol fatty acid esters are natural oils and fats, e.g. coconut oil, palm oil; tripalmitate, tristearate, and tribehenate of glycerol; and the like. A particularly preferable example is triglycerol fatty acid ester produced from two behenic acids and one oleic acid (Japanese Patent Laid-open No. 210017/1986).

The ratio by weight of dextrin fatty acid ester and glycerol fatty acid ester to be incorporated in the composition of the present invention is from 9:1 to 4:6 in general and preferably from 8:2 to 1:1. The ratio out of the range of 9:1-4:6 gives an adverse effect on characteristics of the composition. For example, if the amount of glycerol fatty acid ester is less than this range, the retentivity of the compound is lowered, while if the amount of dextrin fatty acid ester is less than the defined range, the transparency of the composition is adversely affected. The total amount of both the fatty acid esters to be incorporated in the composition of the present invention is preferably 2-75% by weight, with 5-50% by weight being particularly preferable. The amount less than 2% by weight results in lowering the adhesive capability and retentivity of the composition, while the amount greater than 75% by weight gives an adverse effect on the adhesive capability and extendibility of the composition.

As the liquid oils used in this invention, any oil which is liquid at 20° C. and those usually used for cosmetic compositions can be used. Given as examples of these oils are hydrocarbons such as liquid paraffin, liquid isoparaffin (liquid polyisobutylene), squalane, and the like; natural animal or vegetable oils and fats such as olive oil, castor oil, jojova oil, and the like; silicone oils such as dimethylpolysiloxane and the like; and synthetic esters such as malate, neopentyl glycolate, isopropyl myristate, and the like. Such oils are preferably incorporated in the composition of the present invention in an amount of 25-98% by weight with 50-95% by weight being particularly preferable.

The transparency of the composition of the present invention can be improved by further adding a branched fatty acid cholesteryl ester, for example, disclosed in Japanese Patent Laid-open Nos. 65809/1981 and 1407/1984. A preferable amount of the branched fatty acid cholesteryl ester to be incorporated is 1-75% by weight with 5-50% by weight being particularly preferable. Water or water-soluble polyvalent alcohol may be incorporated in the composition of the present invention as required to the extent that the transparency of the compound are not impaired. The water-soluble polyvalent alcohols used in this invention are those having two or more of a hydroxyl group in a molecule. Given as examples of these alcohols having two hydroxyl groups are dipropylene glycol, 1,3-butylene glycol, 1,4-butylene glycol, and the like. Examples of the water-soluble polyvalent alcohols having three or more of hydroxyl groups are polyglycerols such as glycerol, diglycerol, triglycerol, tetraglycerol, and the like; maltose, maltitol, sucrose, fructose, xylitol, sorbitol, maltotriose, threitol, erythritol, and the like.

Other than the above essential components, various known components used for compositions for external application can be incorporated in the oily compositions for external application of the present invention as required. Such components include antioxidants, powders, surfactants, antiseptics, perfumes, coloring materials, medicaments, cold sense-promoting agents, UV-ray absorbents, and the like.

The oily compositions for external application of the present invention can be used as an oil phase for various emulsion compositions.

Other features of the invention will become apparent in the course of the following description of the exemplary embodiments which are given for illustration of the invention and are not intended to be limiting thereof.

EXAMPLES

Example 1

Ingredients of each composition shown in Table 1 were dissolved homogeneously under heat and cooled to room temperature to obtain each oily composition (i.e., lip creams).

Transparency, retentivity, extendibility, and adhesive capability of each oily composition obtained were evaluated according to the standard shown below. FIG. 1 shows the results.

Evaluation Standard

The evaluation of each composition was performed according to the following criteria using Comparative Composition B as a standard.
CCC: Normal
BBB: Good
AAA: Very good

TABLE 1

| | % by weight | | | | |
|---|---|---|---|---|---|
| | Invention Composition | | | Comparative Composition | |
| | 1 | 2 | 3 | A | B |
| Component | | | | | |
| Carnauba wax | — | — | — | 4 | — |
| Ceresine | — | — | — | 4 | — |
| Candellila wax | — | — | — | 5 | — |
| Microcrystalline wax | — | — | — | 4 | 10 |
| Glycerol monopalmitate | 5 | — | 5 | — | — |
| Oleic acid dibehenic acid triglyceride | — | 10 | 10 | — | — |
| Dextrin palmitate (Leopal KL by Chiba Seifun Co.) | 15 | 4 | 20 | — | 10 |
| Dextrin stearate | — | 4 | — | — | — |
| Liquid paraffin | 48 | 17 | 10 | 33 | 80 |
| Octyldodecyl myristate | 32 | 65 | 25 | 50 | — |
| Cholesteryl stearate | — | — | 30 | — | — |
| Evaluation | | | | | |
| Transparency | BBB | BBB-AAA | AAA | CCC | CCC |
| Retentivity | BBB | BBB | AAA | CCC | CCC |
| Extendibility | BBB | BBB-AAA | AAA | CCC | CCC |
| Adhesive Capability | BBB | BBB | AAA | CCC | CCC |

Example 2

The four components shown below were dissolved under heat and homogeneously mixed. The mixture was cooled to room temperature to obtain an oily composition for external application (i.e., antiphlogistic). In this example, various oily compositions for external application were prepared using as an oil component squalane, liquid paraffin having medium viscosity, neopentyl glycol dicaprate, isopropyl myristate (IPM), 2-ethylhexanic acid triglyceride, olive oil, jojova oil, myristic acid isostearic acid diglyceride, diisostearyl malate respectively.

| Components: | |
|---|---|
| Dextrin palmitate (Leopal KL) | 12 g |
| Oleic acid dibehenic acid triglyceride | 3 g |
| l-menthol | 1 g |
| Oil | 84 g |
| Total | 100 g |

Every oily composition for external application using the above oil components respectively exhibited excellent transparency, retentivity, extendibility and adhesive capability.

Example 3

Ingredients of each composition shown in Table 2 were heated to 100° C. and homogeneously mixed. The mixture was cooled to room temperature to obtain a face powder. The results are shown in Table 2.

TABLE 2

| Component | % by weight Invention Composition | |
|---|---|---|
| | 4 | 5 |
| Oleic acid dibehenic acid triglyceride | 1 | 12 |
| Dextrin myristate | 9 | 8 |
| Titanium oxide | 5 | 5 |
| Sericite | 25 | 25 |
| Talc | 5 | 5 |
| Kaolin | 10 | 10 |
| Squalane | 15 | 5 |
| Methylphenylpolysiloxane | 5 | 5 |
| Olive oil | 15 | 15 |
| Jojova oil | 5 | 5 |
| Isopropyl myristate | 5 | 5 |

The oily foundations obtained exhibited excellent retentivity, extendibility, and adhesive capability.

Example 4

The components shown below were processed in the same manner as in Example 3 to obtain an oily mascara.

| Components: | % by weight |
|---|---|
| Oleic acid behenic acid triglyceride | 6 |
| Dextrin palmitate | 5 |
| Titanium oxide | 5 |
| Sericite | 2 |
| Talc | 1 |
| Pigment | 2 |
| Liquid paraffin | 39 |
| Olive oil | 40 |
| Total | 100 |

The oily mascara obtained had excellent retentivity, extendibility, and adhesive capability.

The oily compositions for external application according to the present invention are transparent or semi-transparent, and possess excellent extendibility, adhesive capability, and retentivity. The compositions are thus useful for various oily cosmetics and oily medicines for external application.

Obviously, numerous modifications and variations of the present invention are possible in light of the above teachings. It is therefore to be understood that the scope of the appended claims, the invention may be practiced otherwise than as specifically described herein.

What is claimed is:

1. An oil composition for external application consisting essentially of (A) a dextrin fatty acid ester, (B) a glycerol fatty acid ester having a melting point of higher than 20° C., wherein (A)+(B)=2-75 wt. % of said composition and the ratio (A):(B) is from 9:1-4:6 by weight, and 25-98 wt. % of (C) a cosmetically acceptable oil which is liquid at 20° C.

2. The composition for external application according to claim 1, wherein said dextrin fatty acid ester (A) is an ester of a dextrin of an average polymerization degree of 10 to 50 and a fatty acid having 8-24 carbon atoms.

3. The composition for external application according to claim 1, wherein said glycerol fatty acid ester (B) has a melting point of higher than 20° C. and a fatty acid residue with a carbon atom content of 8-22.

4. The composition for external application according to claim 2, wherein said dextrin has an average polymerization degree of 20-30.

5. The composition for external application according to claim 1, wherein the ratio (A):(B) is from 8:2 to 1:1.

6. The composition for external application according to claim 1, wherein (A)+(B)=5-50 wt. % of said composition.

7. The composition for external application according to claim 1, comprising 50-95 wt. % of said cosmetically acceptable oil.

8. An oil composition for external application consisting essentially of (A) a dextrin fatty acid ester, (B) a glycerol fatty acid ester having a melting point of higher than 20° C., wherein (A)+(B)=2-75 wt. % of said composition and the ratio (A):(B) is from 9:1-4:6 by weight, 25-98 wt. % of (C) a cosmetically acceptably oil which is liquid at 20° C. and (D) 1-75 wt. % of a branched fatty acid cholesteryl ester.

9. The composition for external application according to claim 8, comprising 5-50 wt. % of said branched fatty acid cholesteryl ester.

10. An oil composition for external application consisting essentially of (A) a dextrin fatty acid ester, (B) a glycerol fatty acid ester having a melting point of higher than 20° C., wherein (A)+(B)=2-75 wt. % of said composition and the ratio (A):(B) is from 9:1-4:6 by weight, 25-98 wt. % of (C) a cosmetically acceptable oil which is liquid at 10° C. and (D) at least one component selected from the group consisting of antioxidants, powders, surfactants, antiseptics, perfumes, coloring materials, medicaments, cold sense-promoting agents and UV-ray absorbents.

11. An oil composition for external application consisting essentially of (A) a dextrin fatty acid ester, (B) a glycerol fatty acid ester having a melting point of higher than 20° C., wherein (A)+(B)=2-75 wt. % of said composition and the ratio (A):(B) is from 9:1-4:6 by weight, 25-98 wt. % of (C) a cosmetically acceptable oil which is liquid at 20° C., 1-75 wt. % of (D) a branched fatty acid cholesteryl ester, and at least one component selected from the group consisting of antioxidants, powders, surfactants, antiseptics, perfumes, coloring materials, medicaments, cold sense-promoting agents and UV-ray absorbents.

* * * * *